United States Patent [19]
von Alfthan et al.

[11] Patent Number: 5,212,994
[45] Date of Patent: May 25, 1993

[54] MEASURING CELL

[75] Inventors: George C. von Alfthan, Kauniainen; Kari O. Mann, Espoo, both of Finland

[73] Assignee: Outokumpu Oy, Helsinki, Finland

[21] Appl. No.: 666,361

[22] Filed: Mar. 8, 1991

[30] Foreign Application Priority Data

Mar. 14, 1990 [FI] Finland ............................... 901257

[51] Int. Cl.$^5$ ............................................ G01N 33/00
[52] U.S. Cl. ......................................... 73/866; 250/438
[58] Field of Search ................. 73/866, 571; 356/440; 250/428, 432 R, 433, 434, 435, 438; 378/66, 67

[56] References Cited

U.S. PATENT DOCUMENTS

| | | | |
|---|---|---|---|
| 3,511,078 | 5/1970 | Rajkai | 73/866 X |
| 3,869,214 | 3/1975 | Egli et al. | 356/246 |
| 3,869,215 | 3/1975 | Nolan | 356/246 |
| 4,108,602 | 8/1978 | Hanson et al. | 73/866 X |
| 4,260,263 | 4/1981 | Kummer | 356/448 |
| 4,274,286 | 6/1981 | Gioia | 73/866 |
| 4,498,338 | 2/1985 | Peltonen et al. | 73/866 X |
| 4,750,837 | 6/1988 | Gifford et al. | 356/318 X |
| 4,777,907 | 10/1988 | Sänger | 198/400 X |
| 4,888,484 | 12/1989 | Harvey | 356/440 X |
| 5,125,279 | 6/1992 | Anthony et al. | 73/866 |

FOREIGN PATENT DOCUMENTS

| | | | |
|---|---|---|---|
| 62733 | 2/1983 | Finland . | |
| 272940 | 10/1989 | Japan | 73/866 |
| 608081 | 5/1978 | U.S.S.R. | 73/866 |
| 634177 | 11/1978 | U.S.S.R. | 73/866 |
| 634178 | 11/1978 | U.S.S.R. | 73/866 |
| 1383154 | 3/1988 | U.S.S.R. | 73/866 |
| 1516894 | 10/1989 | U.S.S.R. | 73/866 |

Primary Examiner—Tom Noland
Attorney, Agent, or Firm—Dellett, Smith-Hill and Bedell

[57] ABSTRACT

The invention relates to a measuring cell for analyzing solid granular or pulverous material, which measuring cell (1) is provided with an aperture (5) in the wall for a measuring window (6). Through the measuring window, the material fed in the measuring cell (1) can be analyzed according to the invention, so that inside the measuring cell (1) there is installed a feeder (10) in order to regulate the essentially continuous material flow passing through the measuring cell (1), and a guide member (8) in order to guide the material flow to pass by essentially near to the measuring window (6).

13 Claims, 1 Drawing Sheet

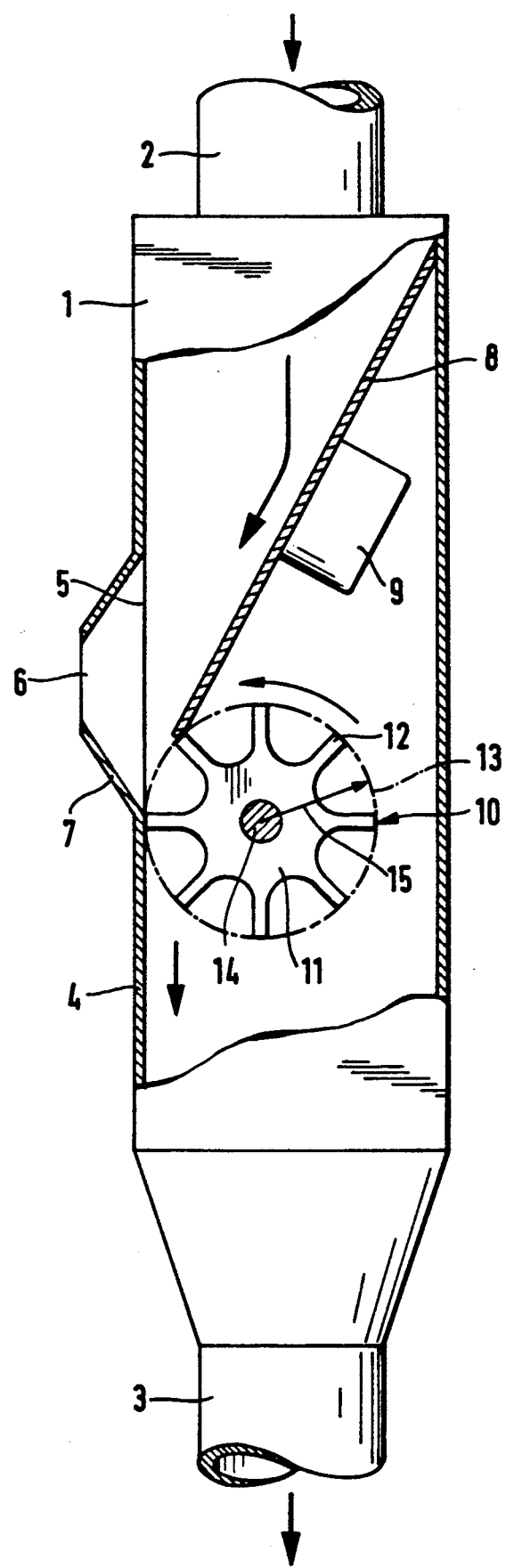

MEASURING CELL

BACKGROUND OF THE INVENTION

The present invention relates to a measuring cell, whereby solid granular or pulverous material is analyzed in order to define the chemical, physical and/or physico-chemical properties of the material.

From the FI patent 62,733 there is known an apparatus for analyzing granular and pulverous material as for its physical or physico-chemical properties, which apparatus comprises a chamber provided with an aperture covered with a radiation-permeable membrane, which chamber can be filled with pulverous or granular material. In this apparatus, the material to be analyzed is fed in through the top part of the chamber, and at the bottom of the chamber there is provided a stop valve and a vibrator, so that the chamber can be tightly filled with the material to be analyzed, at least as high as the top part of the aperture covered with the membrane, prior to the analysis. This is carried out by closing the valve for the duration of the filling, and at the same time by keeping the vibrator in operation in order to pack the material tightly. Consequently the material in question remains stable during analysis, and the material flow passing through the chamber is stopped. According to the FI patent 62733, the properties of the material can be analyzed while the material does not move. However, if the apparatus of the FI patent 62,733 is positioned for instance in a main product flow, it is clear that the product flow becomes discontinuous and thus difficult to control.

While employing the apparatus of the FI patent 62,733, the properties of the material under analysis are measured only from the amount of material that happens to fall behind the membrane-covered aperture at certain intervals. The obtained measuring results do not, however, necessarily represent the average properties of the whole amount of material.

SUMMARY OF THE INVENTION

The object of the present invention is to eliminate some of the drawbacks of the prior art and to achieve an improved measuring cell for analyzing granular or pulverous material, in which cell the material to be analyzed can be kept in motion during the analysis. Thus the material flow through the measuring cell is essentially continuous, and the analysis does not cause the material flow to discontinue. The essential novel features of the invention are apparent from the appended patent claims.

The measuring cell of the invention is provided with a measuring window, wherethrough the properties of the material to be analyzed are defined, for instance by means of irradiation. Through the measuring window, it is also possible to examine the radiation emitted by the material itself. Advantageously the measuring cell is so positioned in the flow of the material to be analyzed, either in the main product flow or in a side product flow, that the material under analysis is fed into the measuring cell through the top part thereof, and conducted out of the measuring cell through the bottom part thereof. Furthermore, inside the measuring cell, essentially near to the detector window, there is arranged a material feeder so that the feeder regulates the volume of the material flow at the measuring window. The feeder used in the measuring cell of the present invention is advantageously for instance a rotary vane feeder, a compartment feeder or a screw feeder. Moreover, in order to guide the material to be analyzed towards the vicinity of the measuring window, inside the measuring cell there is arranged a guide member, which is further provided with a vibrator member, which can, if necessary, be used for packing the material tight at the measuring window, or for improving the material flow for instance with such materials that easily stick to the guide member.

According to the invention, the material to be analyzed, which is fed in through the top part of the measuring cell, is directed, by using the inclined guide member, to proceed towards that wall of the measuring cell where the measuring window is located. Thus the material flow coming into the vicinity of the measuring window is regulated by means of the feeder, so that the material passes by the measuring window at an essentially low velocity.

By employing the measuring cell of the present invention, the material passing by the measuring window can be analyzed without essentially interrupting the material flow. Thus, according to the invention, the material can be advantageously analyzed in continuous operation.

In the measuring cell of the invention, by means of the guide member and the feeder, the material flow passing by the measuring window also is regulated by changing the angle of inclination of the guide member and the operating periods and/or structure of the feeder. However, while adjusting the material flow and its velocity, it must be observed that the accuracy of the material analysis is dependent on the material flow employed, and particularly on the velocity thereof. By regulating the material flow and its velocity, the packing density depending on the material in question, which is essential with respect to the accuracy of the analysis, is maintained advantageous.

BRIEF DESCRIPTION OF THE DRAWINGS

The invention is explained in more detail below, with reference to the appended drawing, which is an illustration of a preferred embodiment of the invention, seen in a partial side-view cross-section.

DETAILED DESCRIPTION

According to the drawing, the top part of the measuring cell 1 is provided with a feed duct 2, and the bottom part thereof is provided with an outlet duct 3, in order to connect the measuring cell to the flow of the material to be analyzed. In the vertical wall 4 of the measuring cell 1, there is formed an aperture 5, where the measuring window 6 is installed. The measuring window 6 is made for instance of a transparent, thin plastic film, which is arranged in the aperture 5 by means of supporting members 7.

In order to guide the material flow entering the measuring cell 1, inside the measuring cell 1 there is arranged, in an inclined position, a guide plate 8, whereby the material flow is directed towards the measuring window 6. Advantageously the guide plate 8 is provided with a vibrator member 9, which is used when there is a need to improve the flowing velocity and packing rate of the material in question.

Inside the measuring cell 1, essentially near to the measuring window 6, there is further installed a rotary vane feeder 10, which regulates the material flow discharged from the measuring cell 1 to the outlet duct 3.

According to the drawing, the rotary vane feeder 10 is formed of a rotary, pinion-like member 11, on the outer circumference whereof there are attached blade-like members 12. The blade-like members 12 form a circular orbit 13. The rotary vane feeder 10 is arranged, with respect to the measuring window 6, so that the rotary axis 14 of the rotary vane feeder is located at a distance corresponding to the radius 15 of the circular orbit 13, formed by the blade-like members, from the wall 16 comprising the measuring window 6 of the measuring cell 1. In addition to this, the rotary vane feeder 10 is installed, in the vertical direction of the measuring cell 1, so that the rotary axis 14 is located essentially at the same height as the bottom edge of the measuring window 6. Thus the rotary vane feeder 10 regulates, by using its blade-like members 12, the material flow discharged from the measuring window 6 for instance by means of its rotational speed or by means of the space volume left in between the blade-like members 12, because, owing to the dimensions between the rotary vane feeder 10 and the measuring cell 1, the operation of the rotary vane feeder 10 has an essential effect on the whole material flow.

It is obvious that in the measuring cell of the invention, there can, within the scope of the appended patent claims, also be used other structural arrangements than the ones described above, for instance as regards the feeder and guide member located inside the measuring cell.

We claim:

1. A measuring cell for analyzing solid granular or pulverous material, which measuring cell has an inlet for admitting material to the measuring cell and an outlet for discharging material from the measuring cell, the inlet and outlet being spaced apart along a predetermined axis, and comprises a wall formed with an aperture, a measuring window fitted in the aperture to allow material in the measuring cell to be analyzed, a feeder disposed inside the measuring cell for regulating essentially continuous flow of material through the measuring cell, a guide plate inclined relative to said predetermined axis for guiding material to flow closely adjacent to the measuring window, and a vibrator member attached to the guide plate.

2. A measuring cell according to claim 1, wherein the feeder is arranged to regulate the flow of material past the measuring window.

3. A measuring cell according to claim 1, wherein the feeder is a rotary vane feeder.

4. A measuring cell according to claim 3, wherein the rotary vane feeder is mounted to rotate about an axis that is substantially perpendicular to said predetermined axis.

5. A measuring cell according to claim 4, wherein the guide plate divides the interior of the measuring cell into an inlet compartment and an outlet compartment, and the feeder regulates flow of material from the inlet compartment to the outlet compartment.

6. A measuring cell according to claim 1, wherein said predetermined axis is vertical and the inlet is above the outlet.

7. A measuring cell according to claim 6, wherein the feeder is a rotary vane feeder including a rotor of a predetermined radius mounted to rotate about a substantially horizontal axis that is at substantially the same height as a lower edge of the measuring window and is spaced from said wall by a distance that is substantially equal to the radius of the rotor, whereby the rotary vane feeder regulates flow of material from the inlet compartment to the outlet compartment.

8. A measuring cell according to claim 7, wherein a lower edge of the guide plate is spaced form the axis of rotation of the rotor by a distance that is substantially equal to the radius of the rotor.

9. A measuring cell for analyzing solid granular or pulverous material, which measuring cell has an inlet for admitting material to the measuring cell and an outlet for discharging material from the measuring cell, the inlet and outlet being spaced apart along a predetermined axis, and measuring cell comprising a wall formed with an aperture, a measuring window fitted in the aperture to allow material in the measuring cell to be analyzed, a guide plate for guiding material to flow closely adjacent to the measuring window, said guide plate being inclined relative to said predetermined axis and dividing the interior of the measuring cell into an inlet compartment and an outlet compartment, and a rotary vane feeder mounted inside the measuring cell to rotate about an axis that is substantially perpendicular to said predetermined axis, for regulating essentially continuous flow of material form the inlet compartment to the outlet compartment.

10. A measuring cell according to claim 9, further comprising a vibrator member attached to the guide plate.

11. A measuring cell according to claim 9, wherein said predetermined axis is vertical and the inlet is above the outlet.

12. A measuring cell according to claim 11, wherein the rotary vane feeder includes a rotor of a predetermined radius mounted to rotate about a substantially horizontal axis that is at substantially the same height as a lower edge of the measuring window and is spaced from said wall by a distance that is substantially equal to the radius of the rotor, whereby the rotary vane feeder regulates flow of material from the inlet compartment to the outlet compartment.

13. A measuring cell according to claim 12, wherein a lower edge of the guide plate is spaced from the axis of rotation of the rotor by a distance that is substantially equal to the radius of the rotor.

* * * * *